US007222540B2

(12) United States Patent
Cross et al.

(10) Patent No.: US 7,222,540 B2
(45) Date of Patent: May 29, 2007

(54) WIRELINE EXTENSOMETER

(75) Inventors: Joseph A. Cross, Tucson, AZ (US);
Daniel J. Lowe, Vail, AZ (US); Paul F. Cicchini, Tucson, AZ (US); Scott T. Broome, Tucson, AZ (US); Paul R. Pryor, Tucson, AZ (US); David E. Nicholas, Tucson, AZ (US)

(73) Assignee: Call & Nicholas Instruments, Inc., Tucson, AZ (US)

( * ) Notice: Subject to any disclaimer, the term of this patent is extended or adjusted under 35 U.S.C. 154(b) by 0 days.

(21) Appl. No.: 10/840,938

(22) Filed: May 7, 2004

(65) Prior Publication Data

US 2005/0247136 A1 Nov. 10, 2005

(51) Int. Cl.
*G01N 3/08* (2006.01)
(52) U.S. Cl. ........................................ 73/826
(58) Field of Classification Search .................. 73/826, 73/784, 862–837
See application file for complete search history.

(56) References Cited

U.S. PATENT DOCUMENTS

| 2,435,266 | A | * | 2/1948 | Brillhart ....................... 73/829 |
| 2,605,055 | A | * | 7/1952 | Scott et al. .................. 242/411 |
| 2,912,607 | A |   | 11/1959 | Duncan |
| 3,276,123 | A |   | 10/1966 | Huggenberger |
| 3,303,368 | A |   | 2/1967 | Cohen et al. |
| 3,606,726 | A | * | 9/1971 | Spertus et al. ................ 53/450 |
| 3,700,941 | A |   | 10/1972 | Duncan |
| 3,803,907 | A | * | 4/1974 | Ryckman et al. ............. 73/800 |
| 3,831,287 | A |   | 8/1974 | Sawdo et al. |
| 3,962,693 | A |   | 6/1976 | Schamblin |
| 3,992,927 | A |   | 11/1976 | Troeh |
| 4,058,010 | A |   | 11/1977 | Woodhouse |
| 4,094,189 | A |   | 6/1978 | Serata |
| 4,122,922 | A |   | 10/1978 | Baermann |
| 4,152,617 | A |   | 5/1979 | Janson |
| 4,159,641 | A |   | 7/1979 | Hawkes |
| 4,239,092 | A |   | 12/1980 | Janson |
| 4,242,915 | A |   | 1/1981 | Herman, III |
| 4,291,581 | A | * | 9/1981 | Jacoby ........................ 73/784 |

(Continued)

OTHER PUBLICATIONS

"*Magnetic Brakes & Clutches*", 19 page brochure from Magnetic Technologies LTD, that includes material on the model 610 product.

(Continued)

*Primary Examiner*—Max Noori
(74) *Attorney, Agent, or Firm*—Lawrence R. Oremland, P.C.

(57) ABSTRACT

A new and useful wireline extensometer is provided that uses a tensioned cable extending between a supply spool and an anchor (e.g. of a type connected to a slope mass), measures movement of the cable to reflect movement of the anchor (e.g. due to movement of the slope mass), and includes a magnetic brake configured to provide a predetermined constant non-frictional braking force on the supply spool. The preferred wireline extensometer is designed to (i) minimize the risk of the extensometer reporting data that suggest slope movement where the slope mass has not moved to an undesirable extent, (ii) measure slope movement at relatively slow rates as well as rapid rates, and to (iii) measure slope mass movements continuously, and in a manner that can be efficiently and effectively communicated to responsible personnel.

16 Claims, 11 Drawing Sheets

U.S. PATENT DOCUMENTS

| | | | |
|---|---|---|---|
| 4,305,299 A | | 12/1981 | Serata |
| 4,364,034 A | * | 12/1982 | Bellatty et al. ............. 340/690 |
| 4,514,905 A | * | 5/1985 | Lutzens ....................... 33/787 |
| 4,712,754 A | * | 12/1987 | Brodie .................... 248/231.9 |
| 4,719,803 A | | 1/1988 | Capelle et al. |
| 5,005,422 A | * | 4/1991 | Ruscev et al. ................ 73/784 |
| 5,058,819 A | | 10/1991 | Lacour |
| 5,207,104 A | | 5/1993 | Enderlin |
| 5,216,922 A | * | 6/1993 | Gustafson et al. ............ 73/784 |
| 5,292,284 A | | 3/1994 | Denk et al. |
| 5,581,139 A | | 12/1996 | Toukola |
| 5,591,919 A | | 1/1997 | Hathaway et al. |
| 5,600,194 A | | 2/1997 | Toukola |
| 5,661,464 A | | 8/1997 | Bilak et al. |
| 6,032,449 A | | 3/2000 | Einsle et al. |
| 6,208,053 B1 | | 3/2001 | Scott |
| 6,564,907 B1 | * | 5/2003 | Sasaki ........................ 187/373 |
| 6,854,337 B1 | * | 2/2005 | Tarara et al. ................. 73/826 |
| 6,872,883 B2 | * | 3/2005 | Ginsburg .................. 174/45 R |
| 6,901,818 B1 | * | 6/2005 | Cheung ................. 73/862.393 |
| 2002/0162477 A1 | * | 11/2002 | Palumbo ....................... 104/87 |

OTHER PUBLICATIONS

"*Installation and Maintenance of Hysteresis Brake/Clutch*", Magnetic Technologies LTD: 2 page document that includes information relating to model 610 product. note: this one has a date of Dec. 11, 2001 so I would insert that in the date box.

"*HD25A Absolute Industrial Rugged Metal Optical Encoder*", US Digital Corporation, 4 page document regarding model HD25A encoder.

* cited by examiner

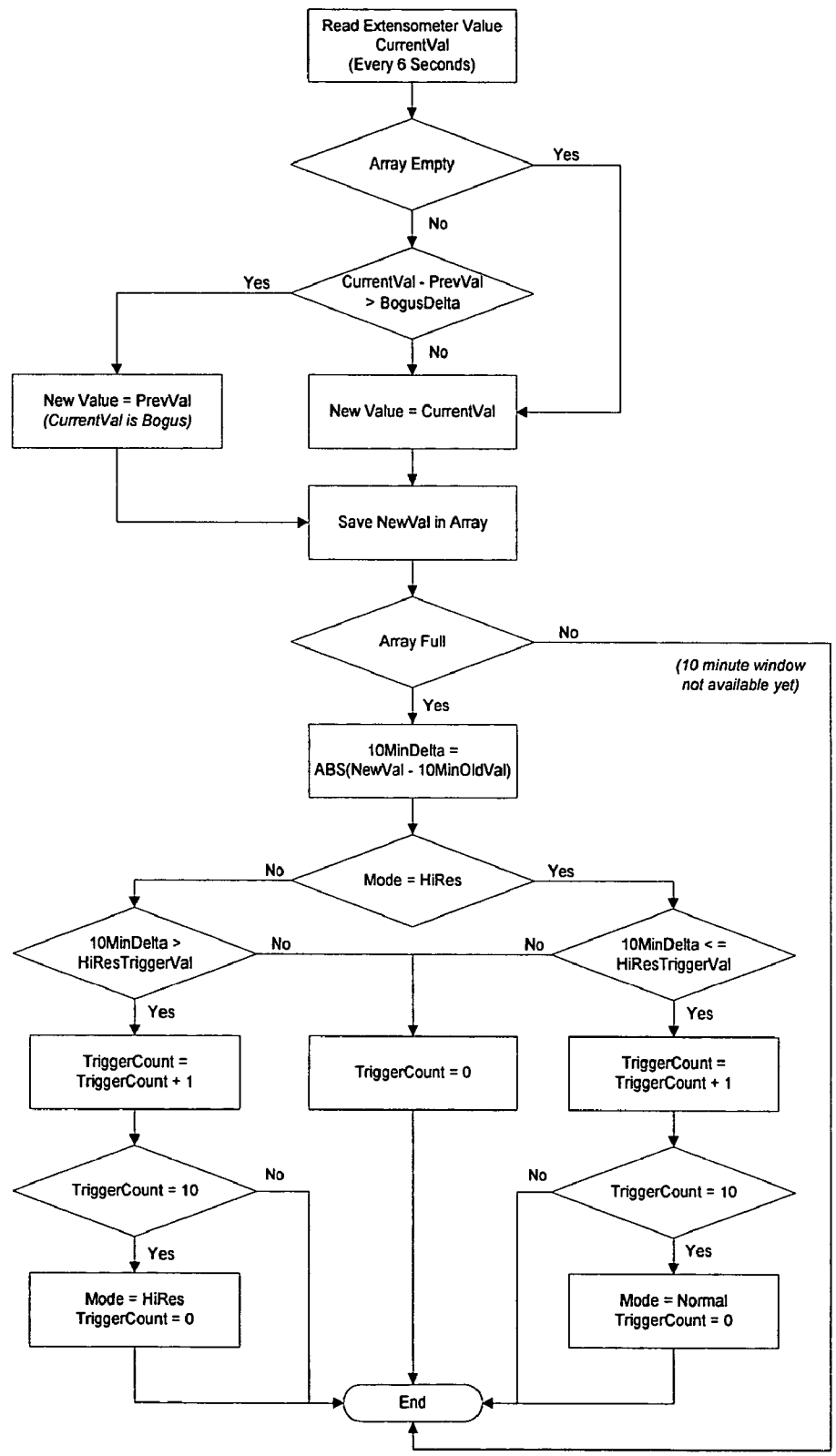
Figure 8a: RSU Extensometer Value Processing

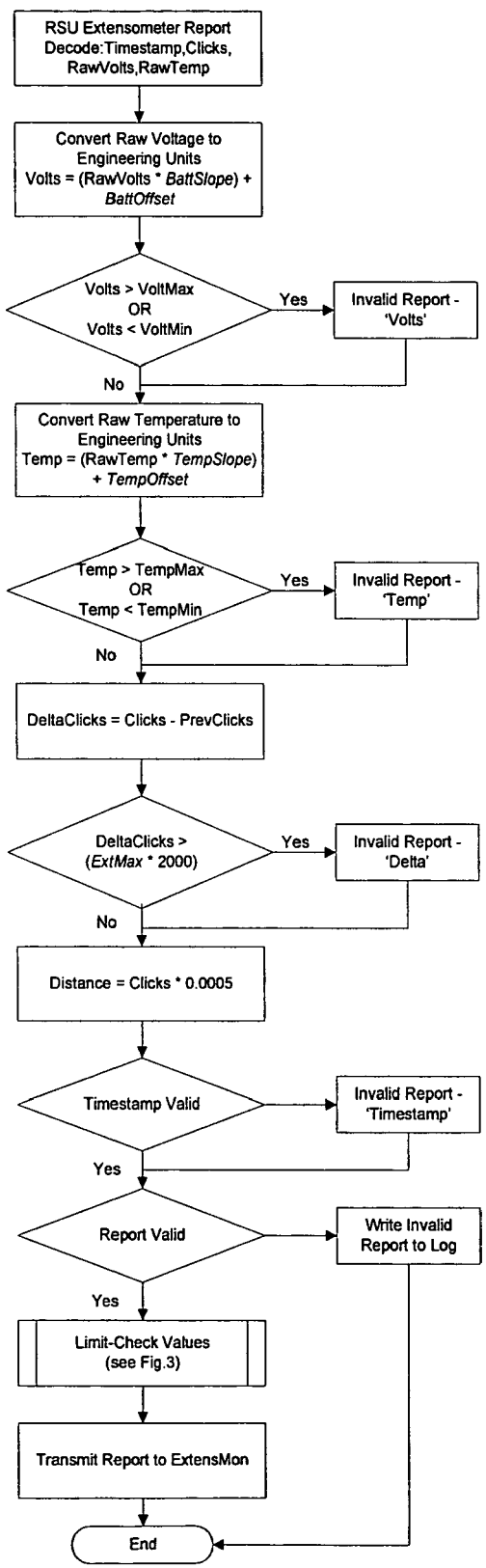
Figure 8b: ExtensBase Extensometer Value Processing

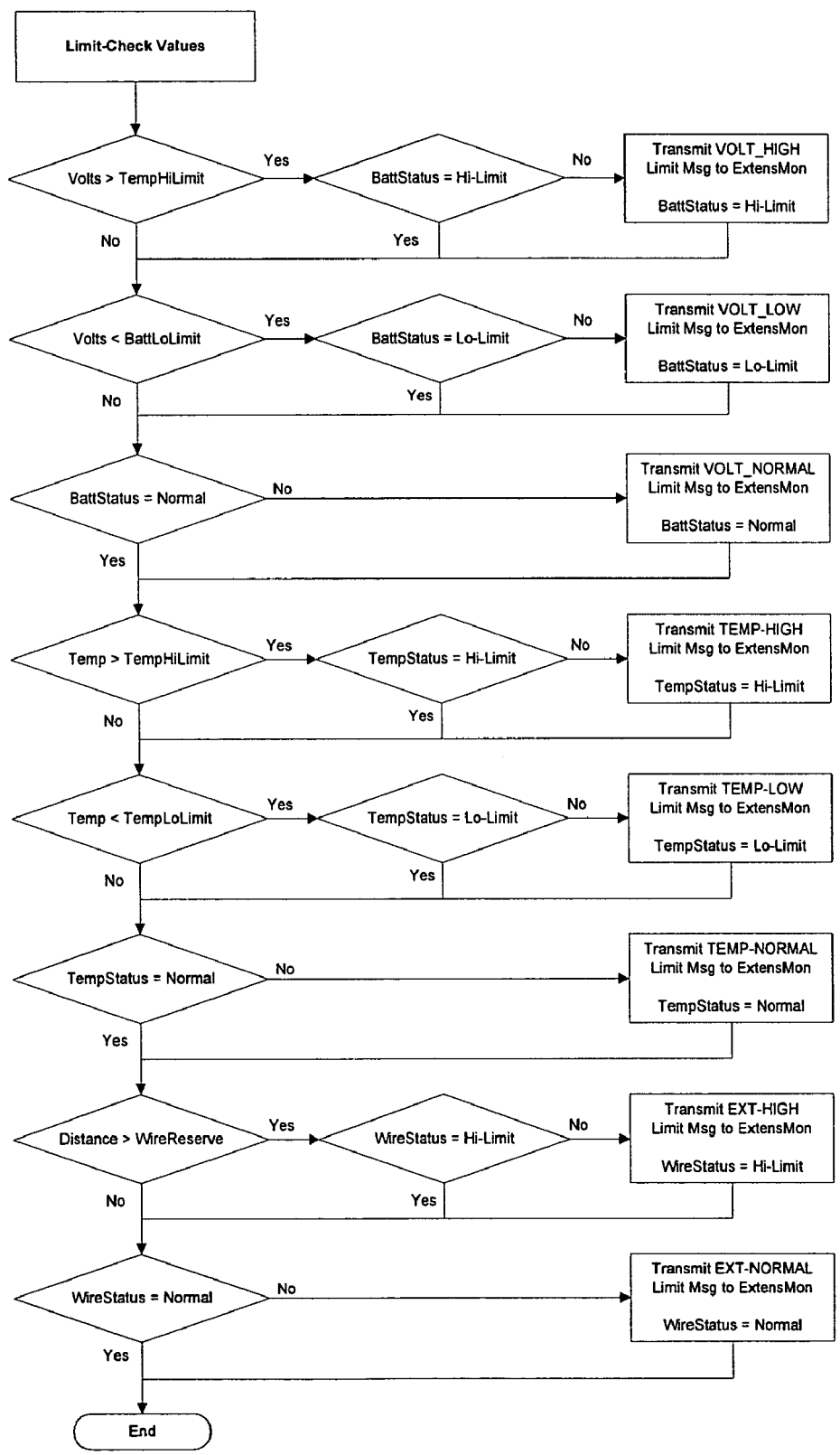
Figure 8c: ExtensBase Extensometer Limit-Check Processing

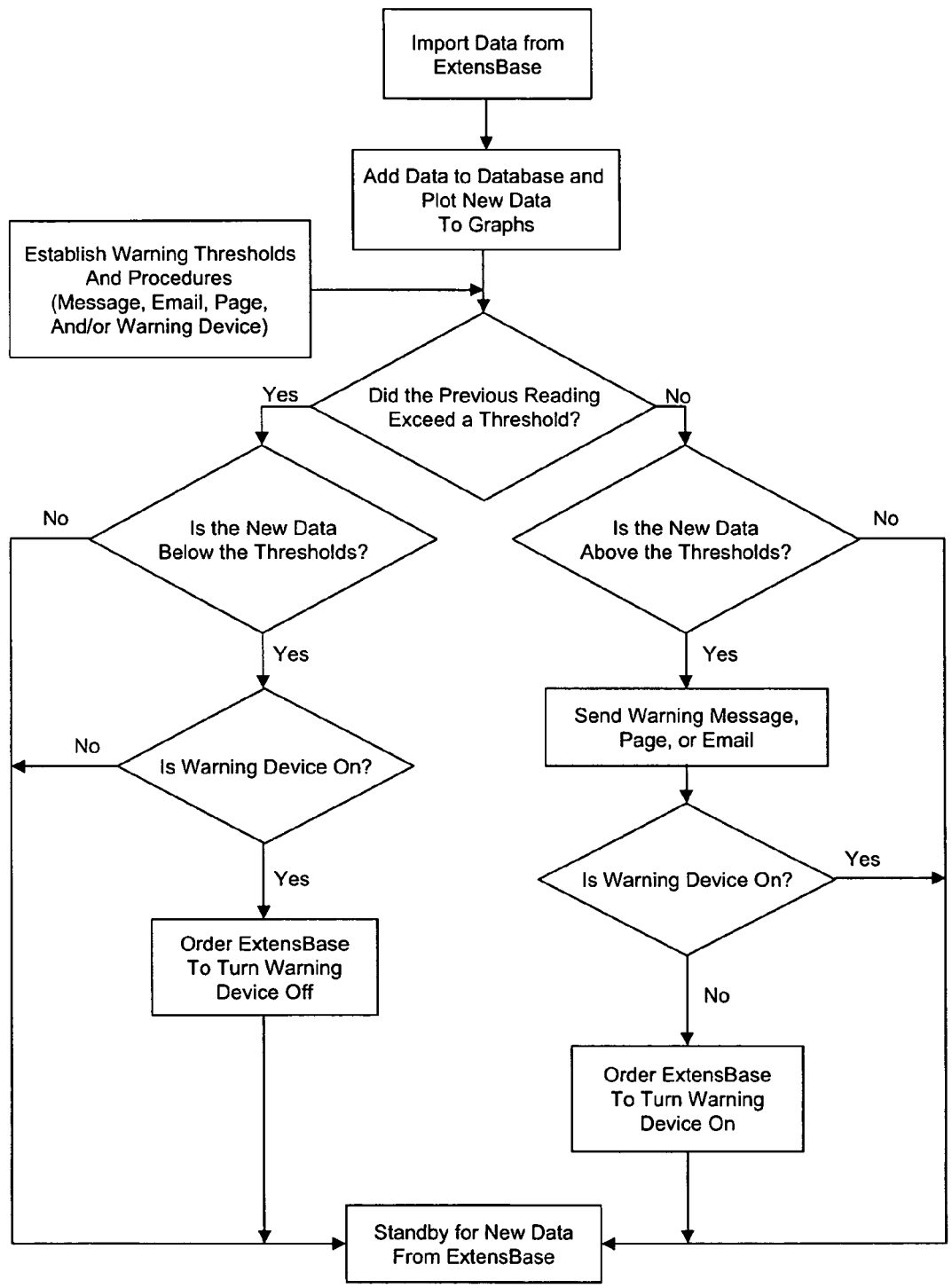
Figure 8d: ExtensMon Warning Threshold Logic

WIRELINE EXTENSOMETER

BACKGROUND

The present invention relates to a new and useful monitoring device, and particularly to a wireline extensometer that is particularly useful in monitoring ground movement, e.g. slopes in an open pit mine environment.

In an open pit mine environment, it is useful to accurately measure movement of a slope mass, in order to identify slope instability, and develop engineering plans to accommodate slope movement or provide for a remediation. In the applicants' experience there is a need for an extensometer that is sensitive to slope mass movement, while minimizing the chance of reporting data that suggest slope movement where the slope mass has not moved to an undesirable extent. In the applicants' experience, it is desirable to measure slope movement at relatively slow rates as well as rapid rates. In addition, in the applicants' experience, it is important to have an extensometer that, as part of a stand alone monitoring system, can measure slope mass movements continuously, and in a manner that can be efficiently and effectively communicated to the responsible personnel.

SUMMARY OF THE INVENTION

The present invention provides a new and useful wireline extensometer that in its preferred form can be incorporated in a system that addresses all of the foregoing issues.

Specifically, the present invention provides a wireline extensometer that uses a tensioned cable extending between a supply spool and an anchor (e.g. of a type connected to a slope mass), which measures movement of the cable to reflect movement of the anchor (e.g. due to movement of the slope mass), and has a magnetic brake that is configured to provide a predetermined constant non-frictional braking force on the supply spool.

Moreover, the preferred wireline extensometer is designed to (i) minimize the risk of the extensometer reporting data that suggest slope movement where the slope mass has not moved to an undesirable extent, (ii) measure slope movement at relatively slow rates as well as rapid rates, and to (iii) measure slope mass movements continuously, and in a manner that can be efficiently and effectively communicated to responsible personnel.

Other features of the present invention will become further apparent from the following detailed description and the accompanying drawings.

BRIEF DESCRIPTION OF THE DRAWINGS

FIGS. 8a–8d schematically illustrate the manner in which data from a slope monitoring device according to the present invention is sampled and processed by a ground monitoring system.

DETAILED DESCRIPTION

As discussed above, the present invention provides a wireline extensometer that uses a tensioned cable extending between a supply spool and an anchor (e.g. of a type connected to a slope mass), measures movement of the cable to reflect movement of the anchor (e.g. due to movement of the slope mass), and has a magnetic brake that is configured to provide a predetermined constant, non-frictional braking force on the supply spool.

The principles of the present invention are described below in connection with a wireline extensometer designed to measure ground movement in a stand alone system of the type that can be used in an open pit mine environment. However, from this description, the manner in which a wireline extensometer according to the principles of the invention can be used in various types of ground monitoring environments will be apparent to those in the art.

Initially, in this application, the wireline extensometer of the invention may be referred to as a Remote Station Unit (RSU). Also, certain software components that form part of the ground monitoring system are referred to as "ExtensBase" and "ExtensMon", as described further below.

Figure 3:
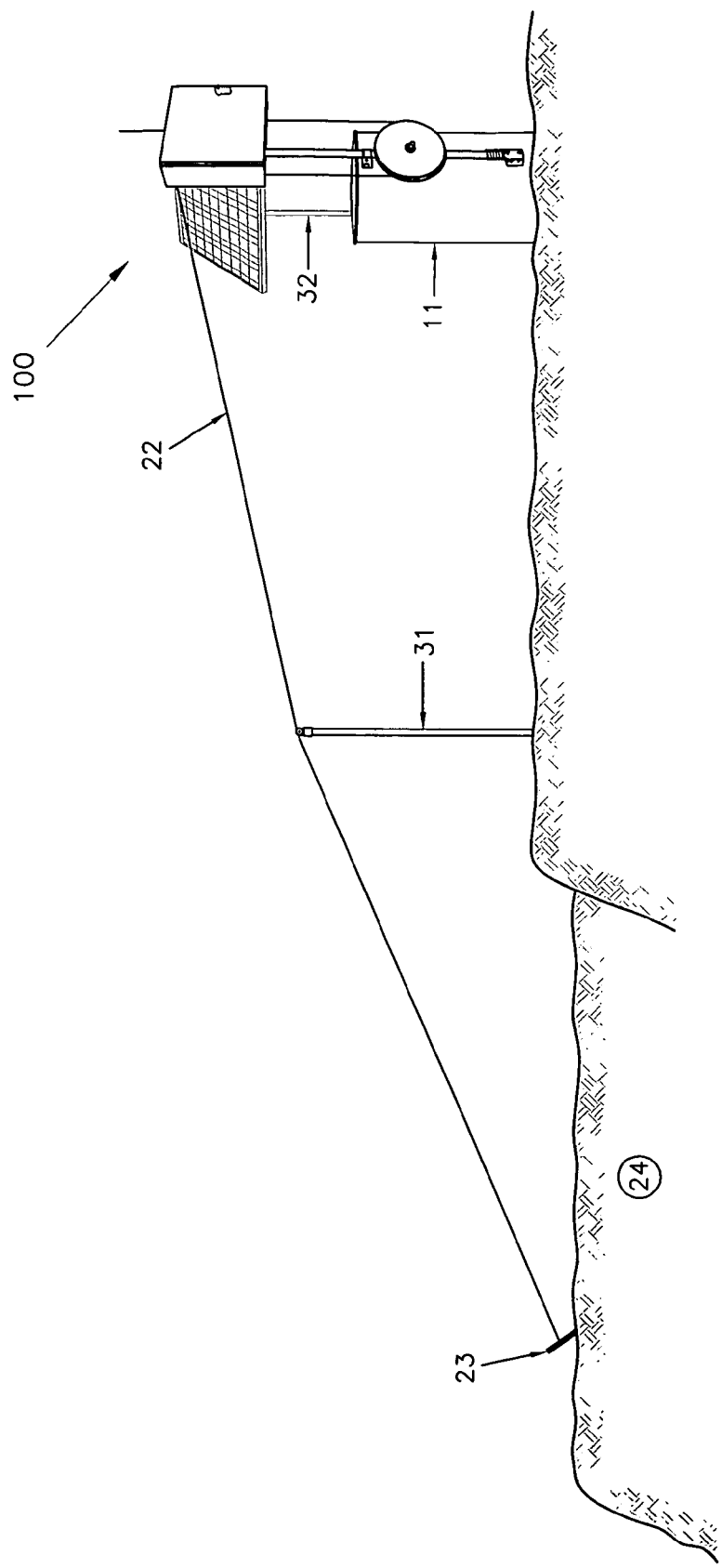
FIG. 3 is a schematic illustration of a wireline extensometer according to the present invention, with a cable extending to a slope that is being monitored.
Figure 4:
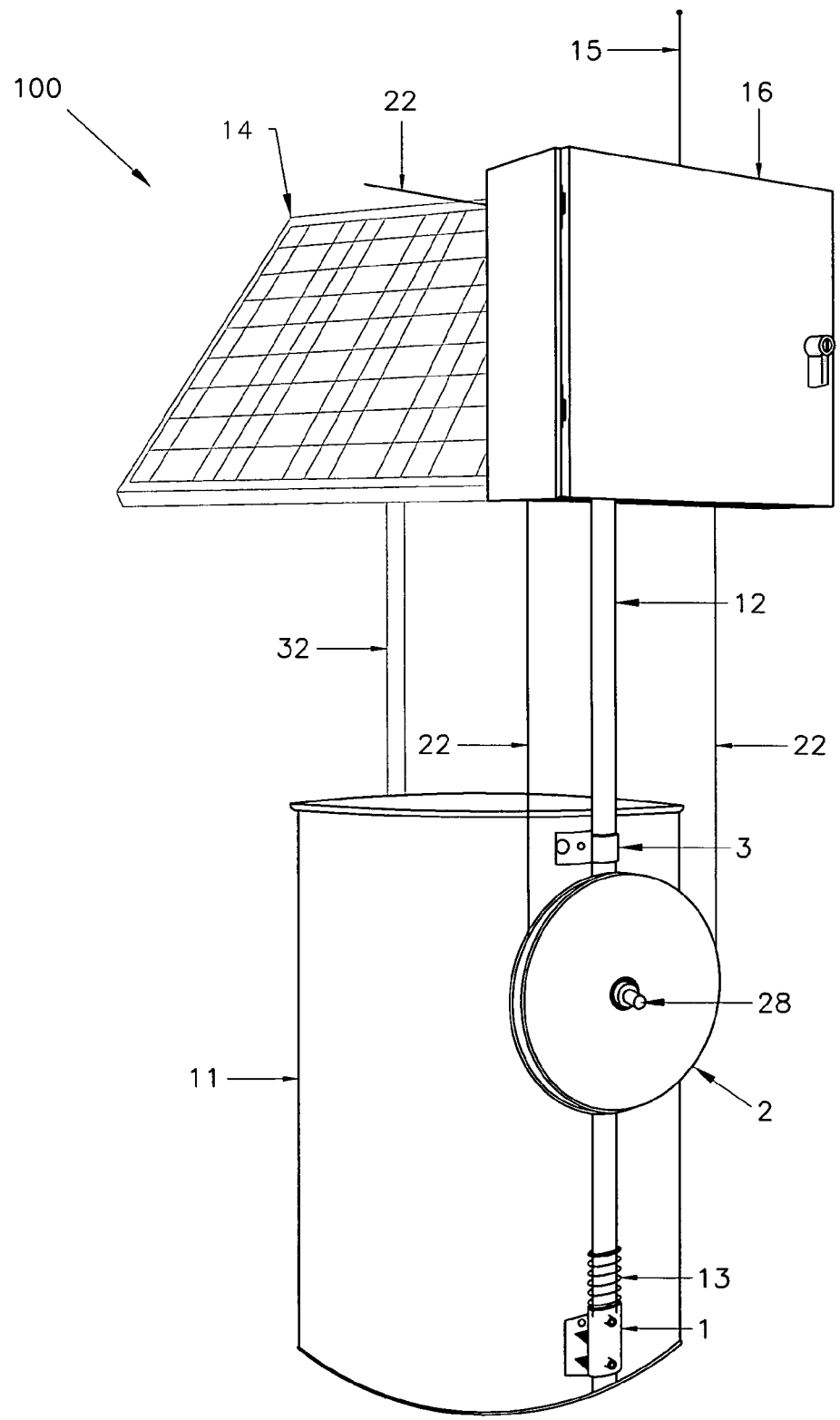
FIG. 4 is a schematic three dimensional view of a wireline extensometer according to the present invention, and showing one version of a support structure and an energy source for the wireline extensometer.
Figure 5:
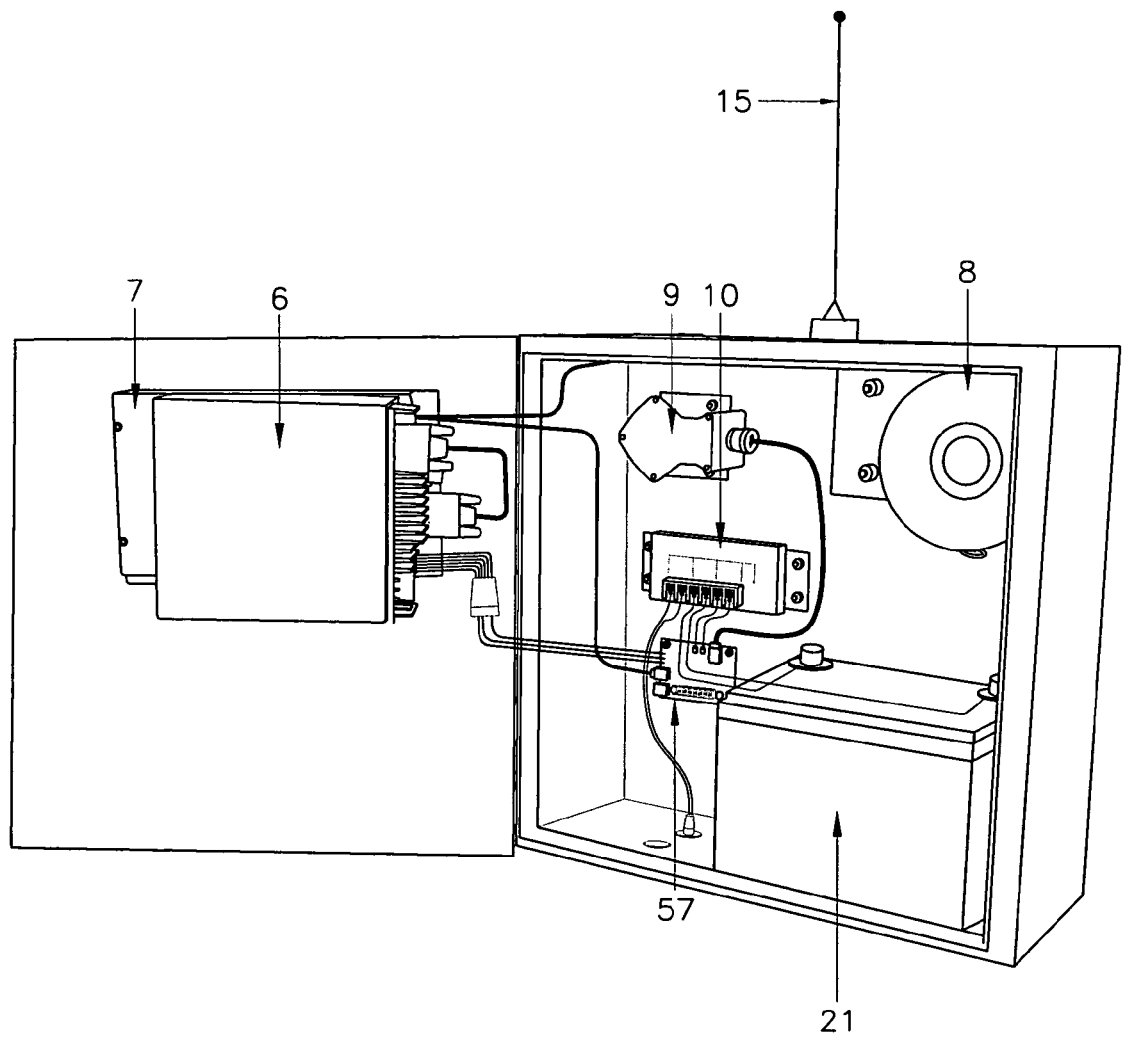
FIG. 5 is a schematic three dimensional view of an enclosure showing certain components of the wireline extensometer according to the present invention, with the enclosure door open.

Referring to the Figures, a wireline extensometer 100 includes a tensioned cable 22 that is wound at one end about the cable supply spool 5, and which has another end connected to an anchor 23 or other connection point on a slope mass 24 (see e.g. FIG. 3). Movement of the slope mass 24 produces movement of the cable 22, and that movement is measured and recorded by the wireline extensometer. One type of environment in which movement of a slope mass is important is an open pit mine environment. Because of the environment, the cable 22 is flexible, multi stranded, and stainless steel to resist corrosion.

Figure 6:
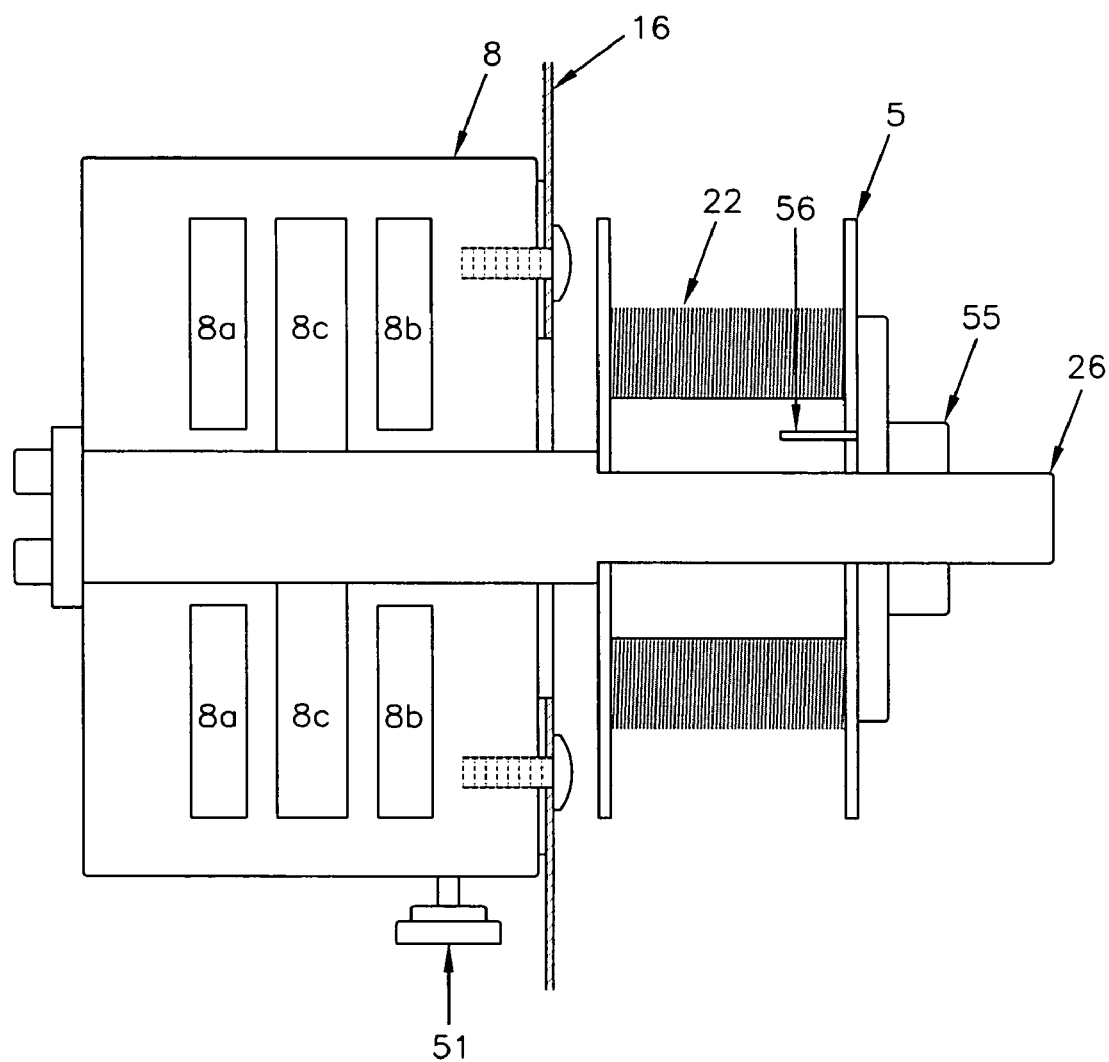
FIG. 6 is a fragmentary cross sectional view of the cable spool and magnetic brake, in a wireline extensometer according to the present invention.

In the illustrated extensometer, the supply spool 5 is located on the outside of an enclosure 16 that is preferably a box that is sealed to a NEMA 4 rating (NEMA is an acronym for the National Electrical Manufacturers Association). The cable supply spool 5 is fixed to a rotatable brake shaft 26 that extends out of the enclosure 16. Specifically, the supply spool is secured on the shaft by a drive plate 55 that clamps to the shaft and drive pin 56 which prevent the spool from turning freely (see FIG. 6). The part of the shaft 26 that is inside the enclosure is connected with a magnetic brake 8, as described further below. Also located on the outside of the enclosure is an encoder sheave 4. The encoder sheave 4 is fixed to a rotatable encoder shaft 27 that extends out of the enclosure. The part of the encoder shaft that is inside the enclosure is connected to an optical encoder 9. The cable 22 extends about the encoder sheave 4 such that movement of the cable due to shifting of the slope mass rotates the encoder sheave 4, and that rotation is measured by the optical encoder 9. That rotation is used to determine the movement of the slope mass, as described further below.

The encoder 9 is preferably a model HD25A made by US Digital Corporation, Vancouver, Wash. The encoder is a non-contacting (zero drag) optical rotary position sensor that reports the shaft angle within a 360° range. The encoder is contained in the NEMA 4 enclosure with only its base and shaft 27 exposed to the elements. The encoder sheave 4, which is a stainless steel sheave, is mounted on the shaft 27, and the cable 22 (which is preferably a multi strand 1×7 stainless steel cable) is wrapped approximately 1.25 turns about the encoder sheave 4 and is then attached to the anchor 23 on the slope being monitored. When the slope moves it rotates the sheave 4 and the optical encoder 9 electronically reports this movement serially to a data logger 7, via an interface such as a US Digital AD-2B converter. The data logger 7 is preferably an Advanced Digital Systems, Tucson, Ariz., Vehicle Logic Module, model VLM-2000.

The enclosure 16 is fixed to a support structure that comprises a steel pipe 12 (which is also referred to herein as a "vertical pipe a vertical support" or a "support pole") connected to a ground support (e.g. a barrel or drum 11). Preferably, brackets 1, 3 or other suitable hardware connect the steel pipe 12 to the enclosure 16 and brackets 1, 3 or other suitable hardware connect the steel pipe to the drum/barrel 11. The drum/barrel 11 can be placed at a desired location in an open pit mine environment, and filled with an appropriate amount of ballast to provide a structural support for the enclosure.

A counterweight sheave 2 is supported by the cable 22 and is vertically moveable along the steel pipe 12. The counterweight sheave 2 is freely rotatable on a shaft 28 that is connected to a sleeve 29 that can move vertically along the steel pipe 12. A coil spring 13 is positioned about the steel pipe 12, and acts between the counterweight sheave sleeve 29 and a bracket 1 near the bottom of the steel pipe, to cushion the counterweight sheave if the counterweight sheave were to drop suddenly.

Figure 1:
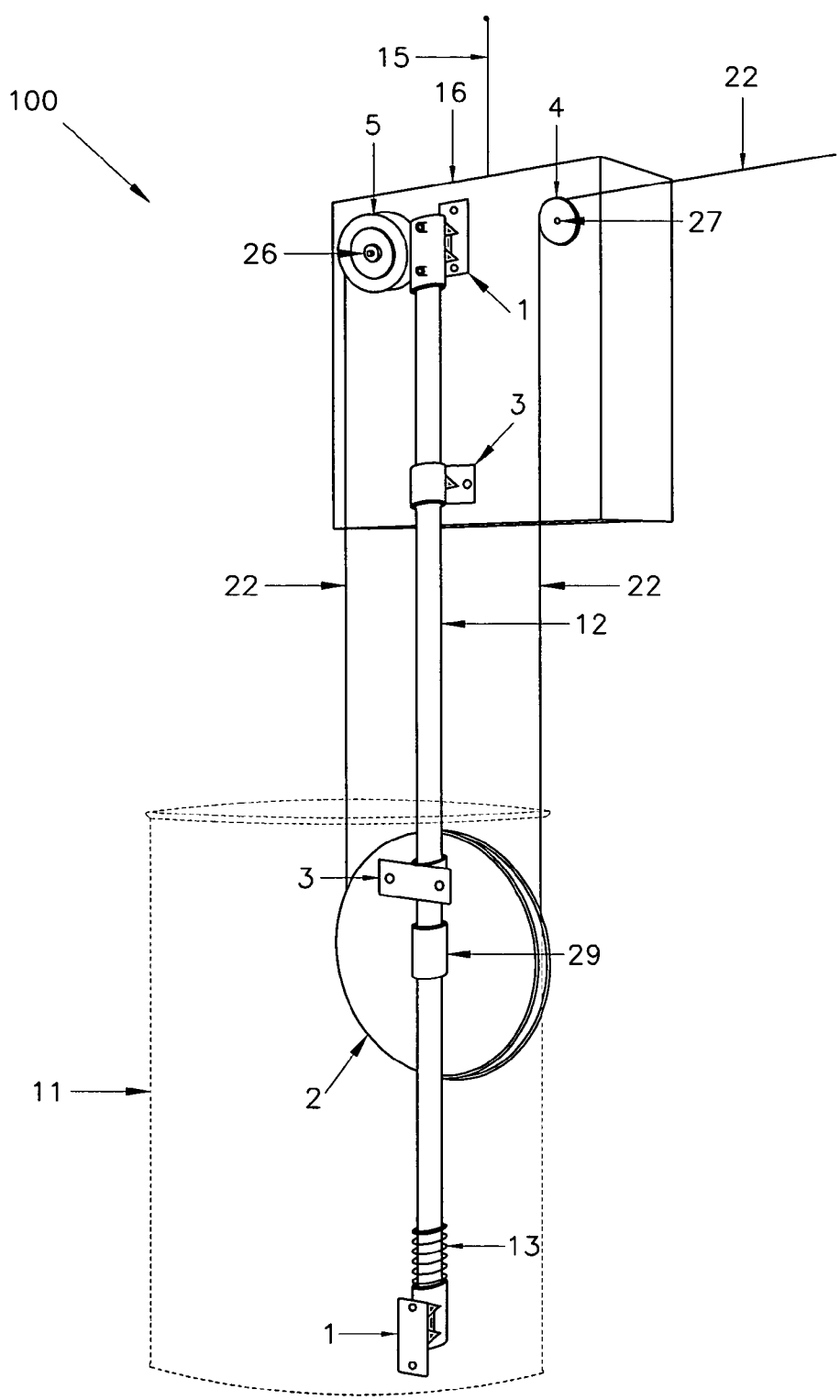
FIG. 1 is a schematic three dimensional illustration of a wireline extensometer, according to the principles of the present invention.
Figure 2:
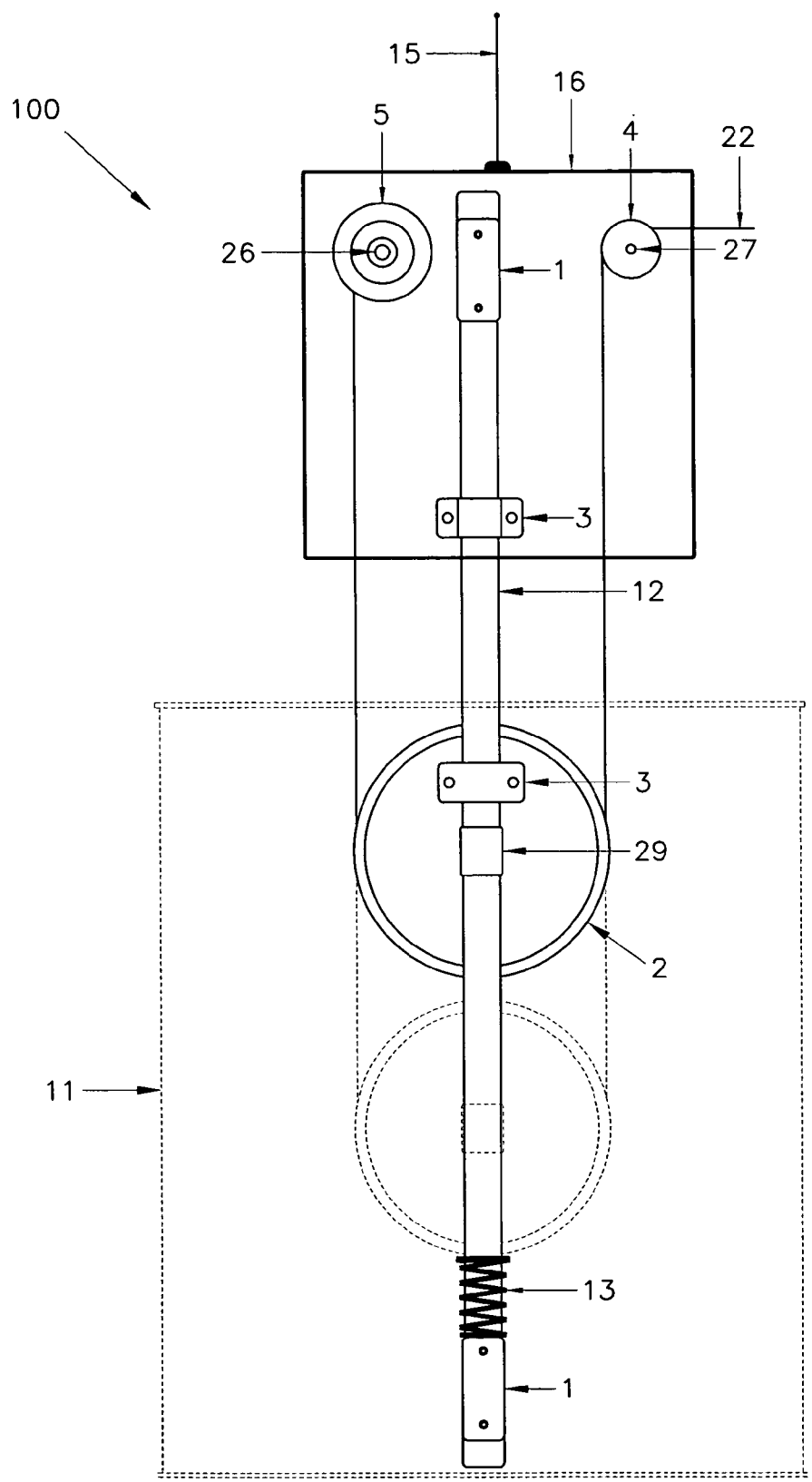
FIG. 2 is a schematic back view of the wireline extensometer of FIG. 1.

The cable 22 is wound about cable supply spool 5, but is not fixedly attached to the cable supply spool. The cable 22 is wound about the counterweight sheave 2, about the encoder sheave 4, optionally over an idler sheave 31 (see e.g. FIG. 3), and then down to the anchor 23 on the slope mass. As can be seen in the figures, the support structure supports the cable supply spool shaft 26 and the encoder shaft 27 in fixed locations and at the same height. The counterweight sheave 2 engages the cable 22 between the cable supply spool 5 and the encoder sheave 4, and since the counterweight sheave can move vertically along the steel pipe 12, the counterweight sheave maintains a minimum amount of tension in the cable 22. Also, because of the foregoing structural relationship between the counterweight sheave 2, the cable supply spool 5 and the encoder sheave 4, the counterweight sheave 2 can take up slack and maintain tension in a length of cable that is up to twice the range of movement of the counterweight sheave 2 along the vertical pipe 12. In FIG. 2, the counterweight sheave 2 is shown in dashed lines near its lowermost position. Also, the spacing between the magnetic brake shaft 26 and encoder shaft 27 is related to the diameter of the counterweight sheave 2 in a manner designed to enable the counterweight sheave 2 to move along the vertical pipe 12 while providing substantially parallel orientation of the cable 22 on opposite sides of the counterweight sheave 2 over the full range of movement of the counterweight sheave 2 along the vertical pipe 12, thereby maintaining a uniform minimum tension in the cable 22.

Moreover, the magnetic brake 8 and the counterweight sheave 2 act in unison to limit the range of tension in the cable 22, thereby minimizing stick-slip behavior, and allowing smooth payout of cable from the cable supply spool 5. In a system that uses friction to control cable payout, stick-slip behavior may result in jerky cable payout due to changes in frictional resistance that occur in the transition from static to dynamic mode. Jerky cable payout can make interpretation of the resulting data difficult. With a wireline extensometer according to the present invention, the magnetic brake is used to avoid introducing friction to control cable payout, to minimize the occurrence of stick-slip behavior.

The wireline extensometer 100 is designed to monitor movement of the tensioned cable 22, as the slope mass 24 shifts, and to transmit data related to such movement to a monitoring system. Movement of the slope mass causes payout of the cable from the cable supply spool 5 and movement of the cable 22 across the encoder sheave 4. This rotates the encoder sheave 4 and the optical encoder shaft 27 connected to the encoder sheave 4. Rotation of the optical encoder shaft 27 is read by the optical encoder 9, in a manner known to those in the art, and that reading is proportional to the movement of the slope mass. The reading is recorded and/or transmitted to a base station 40 or other receiving device (FIG. 7), to provide the responsible personnel with information about movement of the slope mass. For example, measurements can be taken by the optical encoder 9, collected by the data logger 7, and transmitted to the base station 40 by a radio modem 6 and an antenna 15 or other suitable transmitter.

As can be appreciated by the foregoing discussion, electrical power is needed for the system components that collect data, process the data and/or transmit the data. The electrical power is provided by a battery 21 that is connected with a solar photovoltaic power module 14. The voltage of the battery is controlled by a voltage regulator 10. The power module 14 is supported by a support member 32 (e.g. a steel pipe) that is connected to the barrel/drum 11 using appropriate hardware components.

Figure 7:
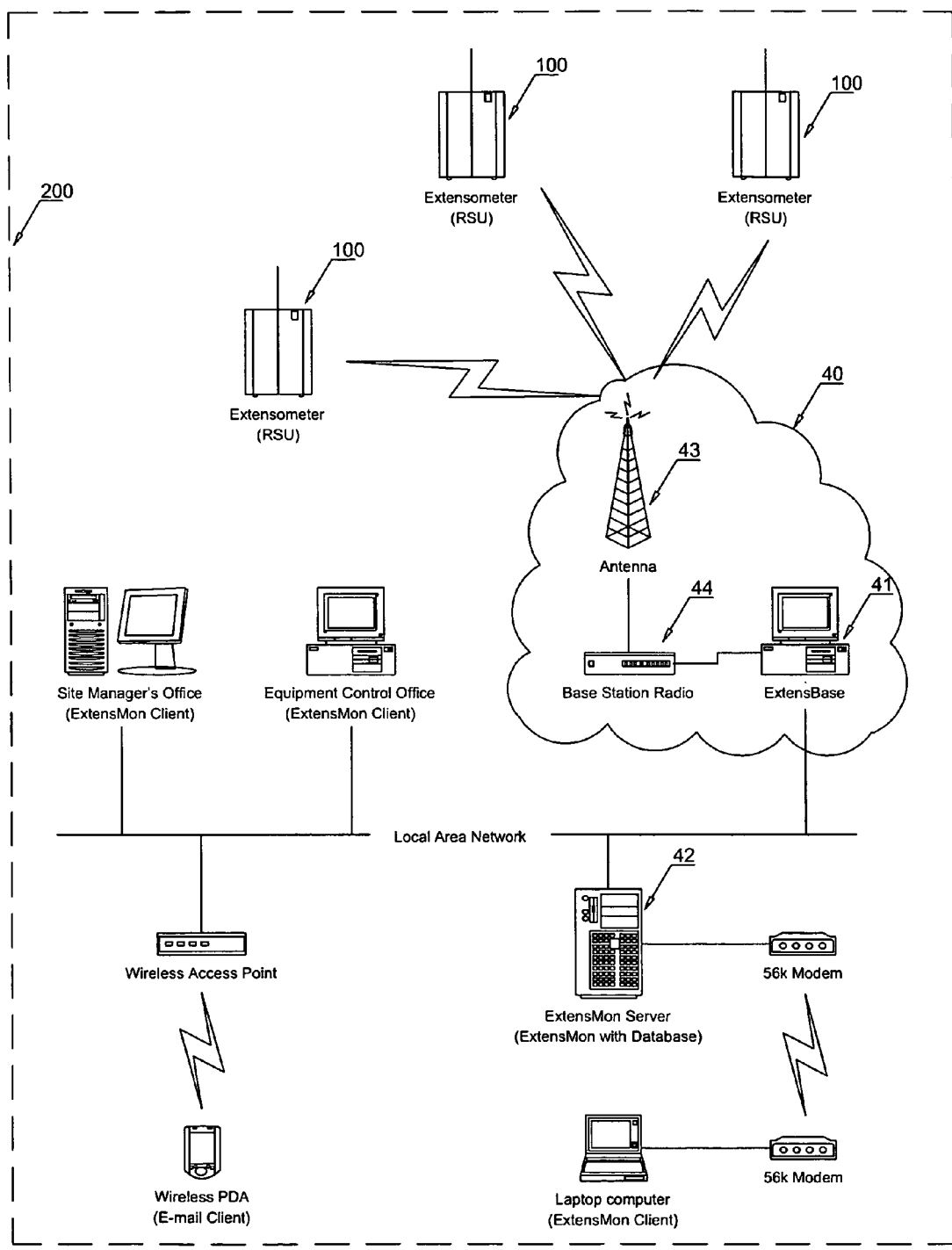
FIG. 7 is a schematic illustration of slope monitoring and communication components that can be used in a ground monitoring system that has one or more wireline extensometers, according to the principles of the present invention.

A ground monitoring system 200 that incorporates RSU's 100 (wireline extensometers) according to the present invention, is shown in FIG. 7. The system is comprised of a base station 40, including software referred to as ExtensBase 41, which resides on a computer as part of the base station 40, and receives telemetry from the RSU via the antenna 43 and base station radio 44. An additional software component, referred to as ExtensMon 42 may reside on the base station computer, or may reside on computers in a network connected with the base station, as schematically shown in FIG. 7.

The ground monitoring system 200 is a stand alone system, in the sense that the system is designed to monitor ground movement, and all components of the system (other than the local area network, if used) are dedicated to measuring, transmitting and compiling ground movement data.

The ExtensBase software 41 communicates with, and controls the sampling interval and data transmission interval of the RSU's via radio telemetry (e.g. via radio modem 6 and antenna 15 on each RSU and an antenna 43 at a base station radio 44). The ExtensBase software 41 relays that movement data to the ExtensMon software 42. The ExtensMon software, compiles the data into a central database where it can be reviewed by the responsible person(s) when necessary. The ExtensMon software 42 compares the incremental movement rate to a threshold established by the responsible person(s). If the incremental movement rate exceeds the predetermined level, the ExtensMon software 42 sends messages via email, pager, or instant messaging to the responsible personnel and can also send a signal to the ExtensBase software 41, to activate remote warning devices (e.g. lights, sirens).

Upon receiving the notification message, the responsible person accesses the ExtensMon software 42 to review movement data.

It should be noted that while the preceding description depicts separate locations for the software components 41 and 42, they can be located on the same computer, preferably at the base station.

In setting up the ground monitoring system, the type of support structure to be used (drum/barrel or permanent) is initially determined. Preferably, a drum or barrel 11 can also be used as a system support that can be set up at one site, and conveniently moved to another site. If a permanent support structure is desired, a steel pipe or column is embedded in a permanent foundation (e.g. a concrete foundation). The vertical steel pipe 12 is attached to the steel pipe or column using appropriate hardware.

Brackets 1, 3 are used to attach the RSU enclosure 16 to the support pole 12. Preferably, the support pole 12 is a one-inch inside diameter schedule 80 galvanized steel water pipe. The NEMA 4 enclosure 16 should be oriented such that when the cable is installed correctly on the wireline extensometer the second end of the cable is directed towards the area of the slope to be monitored as illustrated in the figures. The solar photovoltaic power module 14 support pole 32 is attached to the drum/barrel 11, on the side opposite from the support pole 12, using appropriate hardware such as elbows, clamps and/or U-bolts.

The sliding counterweight sheave 2 is installed on the vertical support pole 12, including a spring coil 13 and washers (where appropriate). The sleeve 29 that supports the shaft 28 of the counterweight sheave 2 is slidably mounted on the pole 12, and adjusted, as necessary, so that counterweight sheave 2 can slide vertically on the pole 12.

The torque setting on the magnetic brake is lowered and the cable 22 is extended to the slope mass 24 to be monitored. The cable is wound around the counterweight sheave 2 one and a half times and then about the encoder sheave 4 one and a quarter times. The second end of the cable 22 is coupled to the anchor 23, which in turn is anchored to the slope mass 24 to be monitored. The magnetic brake setting is then adjusted to approximately 50 percent. The extensometer should be placed far enough from the slope mass being monitored such that the equipment will not be damaged if excessive ground movement occurs. The cable 22 is preferably disposed on the idler sheave 31, such that the cable does not contact the slope being monitored.

The spacing between the magnetic brake shaft 26 and the encoder shaft 27 is related to the diameter of the counterweight sheave 2 in a manner designed to enable the counterweight sheave to move along the vertical support 12 while providing substantially parallel orientation of the cable 22 on opposite sides of the counterweight sheave over the full range of movement of the counterweight sheave along the vertical support, thereby maintaining a uniform minimum tension in the cable. If the parallel relationship of the cable is not maintained, cable tension will fluctuate as the counterweight sheave traverses its vertical travel. Variable tensioning of the cable 22 between the magnetic brake shaft 26, counterweight sheave 2, the encoder shaft 27, and the anchor pin 23, can adversely affect the quality of the data that is recorded.

The magnetic brake 8 is preferably a magnetic hysteresis brake of a type (Model 610) manufactured by Magnetic Technologies LTD, Oxford Mass. This brake model is appropriate to control the counterweight sheave 2, which has an approximate weight of 27 pounds. The torque in the magnetic brake 8 is provided by circular magnets 8a, 8b placed at predetermined locations within the brake housing, and a magnetic hysteresis disc 8c fixed on the shaft 26. The circular magnets 8a, 8b are located opposite each other and on opposite sides of the magnetic hysteresis disc 8c. Each magnet is polarized into quadrants, with alternating quadrants as either positive or negative. When the magnets are positioned so that opposite poles are across from each other, there will be a minimum braking torque on the magnetic hysteresis disc 8c. When the magnets are positioned so that like poles are across from each other, there will be a maximum braking torque on the magnetic hysteresis disc 8c. The brake 8 functions to maintain enough tension on the extensometer cable 22 to keep the counterweight sheave 2 elevated. The adjustment procedure for the magnetic brake is as follows: (i) rotate the brake housing until the percentage of torque is close to 50 percent on the tensioning scale labeled on the brake housing, (ii) adjust the percentage of torque until there is just enough to maintain the counterweight sheave 2 in an elevated position (this is the critical torque percentage) (iii) adjust the counterweight sheave 2 so the setting is at the critical torque percentage plus ten percent and (iv) lock the brake housing in that position by tightening the two set screws 51. This procedure determines the constant non-frictional braking force on the cable supply spool 5. This setting is adjustable in order to account for variable lengths of cables and other environmental conditions, to change the predetermined constant non-frictional braking force on the cable supply spool 5.

The magnetic brake 8 allows cable payout at relatively small increments and incremental rates. The wireline extensometer as described herein can measure ground movement at rates as slow as 0.5 inch per day within a 1 hour time interval (i.e. 0.02 inch per hour, or 0.00006 RPM), and in excess of 150 inches per day (i.e. 6.25 inch per hour, or 0.02 RPM). Typical applications of magnetic brake technology are greater than 2 revolutions per minute, which is much higher than the range of rates described for this wireline extensometer. The magnetic brake does not require power, and therefore reduces the overall electrical consumption of the system. Compared to friction brakes and clutches, the magnetic brake provides an essentially frictionless braking control of the cable supply spool. This feature greatly reduces stick-slip behavior which is discussed above in paragraph 0024. The frictionless magnetic brake does not wear and generate dust within the confines of the NEMA 4 enclosure 16, which can become problematic for the electronic components contained therein.

The battery 21 is connected to the voltage regulator 10. The antenna coaxial cable is plugged into the radio modem 6. A circuit board 57 is designed to reduce the wiring and overall number of parts, for simplicity and reliability, and consists of an (i) encoder interface, (ii) power distribution, (iii) power filtering, (iv) self-resetting fuses, (v) power relays, and a (vi) power switch.

The ExtensBase software 41 controls the radio communications and collects the data from the RSU's. The data is relayed to the ExtensMon software 42 which compiles the data into a database. ExtensMon is the primary interface for setting ground movement thresholds and notification protocols. The software programs ExtensBase and ExtensMon can be run on the same computer or with a local area network (LAN) on separate computers.

Minimum Computer Requirements. The computer used for the base station (or for running either of ExtensBase or ExtensMon software) should be at least 500 MHz with 256K memory. The operating system should be Windows 2000 or XP. The base station software requires a 500 MHz computer with at least 256K memory and Windows 2000 or XP operating system. If a Global Positioning System (GPS) receiver will be used to keep time, then two 9-pin serial ports will be needed. Otherwise, there are several programs available that will update the CPU clock from the Internet.

General Location of Base Station Radio Antenna. The preferable location for the base station antenna 43 is in line-of-sight to the extensometer(s) 100. The base station 40 should be easily accessible or included in a local area network (LAN) so that the data can be easily accessed elsewhere.

In one example of a base station setup, the cable for the base station antenna 43 is 75 feet long. The GPS antenna cable is 25 feet long. If a GPS receiver will be used, the base station computer must be within 25 feet of the GPS antenna. The radio antenna should be mounted such that the bottom of the antenna should be not less than two feet above the roof line. The GPS antenna, if used, can be mounted to any flat surface with an unobstructed view of the sky, such as directly on the roof. With some customizing, it can be mounted on the same strut as the radio antenna to reduce likelihood that it will be covered by snow. A radio modem 44 at the base station 40 can be placed directly on the desk with the computer, or mounted to a nearby wall. The base station antenna polyphaser is then grounded, and the antenna cable and the radio modem cable are connected to the polyphaser. Thus, in the event of a lightning strike on the base station antenna, the polyphaser should prevent the electrical surge from reaching the radio modem and the computer. The radio modem 44 is connected to the base station computer via a serial port. The GPS receiver can be placed on the same desk as the computer. The GPS antenna cable can be plugged into the receiver box, and the receiver box connected to a second serial port on the computer. The radio modem 44 should only be powered up after the antenna 43 has been connected.

SYSTEM OVERVIEW: Ground movement in and around open pit mines can be monitored and measured. A system with extensometers according to the present invention addresses this problem by providing near real-time monitoring of ground movement. When ground movement exceeds a pre-determined threshold the system notifies the responsible personnel.

The system 200 (FIG. 7) comprises a number of hardware and software components. Hardware components include one or more RSU's, base station radio, and base station computer(s). Software components include ExtensBase and ExtensMon which archives and is used to analyze the ground movement data.

Each RSU is a remote monitoring device that measures ground movement and uses radio telemetry to report ground movement to the base station 40. All of the RSU's installed in the system communicate with the base station 40. If communication with the base station is interrupted, an RSU can store movement data until the communication is reestablished. The base station radio 44 is connected by a serial cable to the base station computer. The ExtensBase program 41 uses the base station radio 44 to receive data from the RSU's and send commands to set RSU parameters such as data reporting intervals. The ExtensBase program 41 relays the data to the ExtensMon program 42.

If communication with the ExtensMon software 42 is interrupted, ExtensBase 41 will store the data until communication between the two software programs is restored.

The ExtensMon software 42 stores the RSU data relayed by ExtensBase 41 into a database. The ExtensMon software 42 also presents the data in an intuitive graphical format and notifies responsible personnel when data exceeds preset limits. ExtensMon software 42 and the ExtensBase software 41 can coexist on the same computer, or they may be located on separate computers on the same network.

SOFTWARE CONFIGURATION: The ExtensBase program must be configured with the correct COM port settings if the base station radio was not installed on the default radio port (COM 1) or the optional GPS receiver was not installed on the default GPS port (COM 2).

The Internet Protocol (IP) addresses for the computers running ExtensBase and the ExtensMon server must be fixed and known before software installation can be completed. When the ExtensMon server is installed, a central database file must be created for storage of data. If an ExtensMon client is being installed, then the program must be given the location of the central database file.

The principal data fields in the ExtensMon software are: (i) time and date of the report, (ii) ground movement, (iii) battery voltage, and (iv) temperature.

It is necessary to configure the ExtensBase program system settings when the program is first installed. Those settings are related to the properties of the system, and the properties of the RSU's forming part of the system. For example, whether units (e.g. length, temperature) are recorded as "Imperial" or "Metric" are system parameters. The correct ports to enable the base station computer to communicate with the base station radio and GPS antennas are also included as system parameters. The appropriate communication ports and IP addresses to enable the base station software (ExtensBase) to properly communicate with the ExtensMon program are system parameters. The properties of the individual RSU's have initial default values that may be edited as required by responsible persons. These settings include: (i). limit thresholds, (ii). sleep mode control, (iii). equipment options, (iv). extensometer sampling interval, and (v). extensometer displacement limit.

SYSTEM LOGIC (FIGS. 8a,8b,8c,8d)

In each RSU 100, the VLM data logger 7 reads the current value from the shaft encoder every 6 seconds, regardless of any user settings or whether the radio 6 is 'sleeping' or not.

Actual values read from the shaft encoder (with a sheave of 6-inch circumference) are in units of $1/12{,}000$ of a single revolution of the shaft, which equates to $6/12{,}000 = 0.0005$ inch per unit (or click).

As it is desirable to measure very small velocities (down to 0.5-inch/day which yields only 0.5 inch/0.0005 inch per click/14,400 6-second intervals per day=0.06944 clicks per 6-second reading), velocities are measured over a 10 minute 'moving window'. The encoder and the wireline extensometer, as described herein, can measure ground movement rates of 0.5 inch per day within a 1 hour time interval (i.e. 0.02 inch per hour).

This 'moving window' is accomplished by saving valid readings into a 101 element first-in-first-out array. When this array is full, the time difference between the first and the last value will be 6×100 seconds=600 seconds or 10 minutes. Using this array, velocities can be checked every 6 seconds by looking at the preceding 10-minute history.

The logic for processing values is illustrated in FIG. 8a. Note that the following constants are used in the calculations:

BogusDelta: A delta value between any two consecutive values that is considered out of the normal operating range. BogusDelta is defined by the software parameter 'ExtMax', located in the RSU data logger 7, which is expressed in units of inches, and converted to clicks by ExtensBase. The default value for BogusDelta=1,200 inches or 2,400,000 clicks.

HiResTriggerVal: A velocity value defined by responsible personnel as 'Hi Res Trigger Velocity' for a specific extensometer. The valid range for HiResTriggerVal is between 0.5 inch to 500 inches per day.

PROCESSING LOGIC (See FIG. 8*a*.)

1. The encoder shaft 27 is read to provide an initial variable that is called CurrentVal and recorded by the data logger 7. This value is the sum total of clicks recorded by the data logger every six seconds and updated into the array at all times (see paragraph 0057). This value is the basis for all displacement measurements.

2. If the array (see paragraph 0057) has any existing values, then the Delta Clicks value is calculated and compared to BogusDelta. If the shaft encoder value is determined to be invalid (bogus), then the previous valid value is substituted. The value is then stored in the array. Using the substitute value for bogus readings maintains the timing integrity of the array.

Once a full set of values is available in the array, then the newest and oldest values are used to calculate the '10 Minute Delta' value, used to check if the current mode needs to be changed to/from HiRes mode. The '10 Minute Delta' value, which is refreshed every six seconds, needs to exceed the HiResTriggerVal value for one minute (10 consecutive six-second readings). Note that a TriggerCount variable is used to implement the requirement that HiResTriggerVal values need to exist for 60 seconds before switching to HiRes mode, and that values need to be at or below HiResTriggerVal value for 60 seconds before switching out of HiRes mode.

ExtensBase Data Value Processing (FIGS. 8*b*, 8*c*)

An extensometer reading message from the RSU contains four pieces of information: (i) a timestamp of the real-time 'Timestamp' that the sample was taken (in Greenwich Mean Time [GMT]), (ii) the movement of the wire in clicks (where 1 click=0.0005 inch), (iii) the battery voltage 'Volts' as a scaled value, and (iv) the RSU internal temperature 'Temp' as a scaled value. ExtensBase extracts these four values from the RSU message and processes them following the logic depicted in FIG. 8*b* and FIG. 8*c*.

The timestamp is checked to ensure that the value: (i). is not set in the future with respect to current real-time (ii). Contains a valid day-of-month value (1~31).

The Volts and Temp scaled units are converted to engineering units (Volts/Degrees) using the configuration file values BattSlope/BattOffset (for Volts) and TempSlope/TempOffset (for Temp). If ExtensBase is configured for metric values then the Temp value is converted from Fahrenheit to Celsius.

The Volts value is checked to ensure that it lies within the bounds of the setup parameters VoltMin and VoltMax. If Volts is outside of these bounds then the report is flagged, is considered to be invalid, and is written to an 'invalid report' log.

The Temp value is checked to ensure that it lies within the bounds of the setup parameters TempMin and TempMax. If Temp is outside of these bounds then the report is flagged, is considered to be invalid, and is written to an 'invalid report' log.

The Extension value is compared to the previous value to provide a 'DeltaClicks' value. This is compared to the setup parameters 'ExtMax'. If DeltaClicks is larger than ExtMax then the report is considered to be invalid and is written to an 'invalid report' log.

The Volts, Temp, and Extension values are checked against ExtensMon High and Low limits (See FIG. 8*c*).

If the report was not invalidated, an Extensometer Reading message is formatted and transmitted to ExtensMon.

ExtensMon Processing (FIG. 8*d*)

The manner in which the ExtensMon software collects and stores data communicated by the ExtensBase software, and interfaces with the ExtensBase software, can be seen from FIG. 8*d*. The ExtensMon software produces the information from which an operator can view and understand the data.

It should also be noted that the data logger 7 in the RSU 100 provides internal data reasonability checks that are designed to minimize false readings originating from outside influences other than ground movements. By design the RSU will enter the High Resolution Mode if the HighResVal is exceeded for 10 observations of six seconds each (1 minute). The data logger will filter out data spikes occurring over intervals of less than 1 minute, and that return to the original baseline. Therefore it is less likely that these data spikes of less than 1 minute will be transmitted to the base station 40, and recorded in the ExtensMon database. This type of event could occur, for example, if a person trips over the cable.

Accordingly, as seen from the foregoing description, the present invention provides a slope monitoring device that is designed to accurately monitor ground movements, and to provide various desirable functions in a ground monitoring environment. With the foregoing disclosure in mind, it is believed that various adaptations of a wireline extensometer system and device, according to the principles of the present invention, will be apparent to those in the art.

The invention claimed is:

1. An apparatus for use in a movement monitoring system, comprising a cable supply spool and a cable having first and second ends, the cable being wound about the supply spool at the first end and connected at the second end to an anchor such that the cable can be tensioned between the supply spool and the anchor and movement of the cable past a sensor can be used to monitor movement of the anchor relative to the supply spool, the supply spool being rotatable in one direction to allow payout of the cable from the supply spool, and the cable payout rate from the supply spool being controlled by a magnetic brake that is connected directly with the supply spool and is configured to provide a predetermined constant non-frictional braking force directly on the supply spool.

2. An apparatus as defined in claim 1, wherein tension in the cable is controlled by a counterweight sheave connected with the cable, the supply spool and the counterweight sheave mounted on respective supports, and the support for the counterweight sheave being moveable relative to the support for the supply spool.

3. An apparatus as defined in claim 2, wherein the magnetic brake is adjustable to allow controlled payout of the cable from the supply spool while limiting the maximum tension in the cable, and to allow payout of the cable at varying relatively small increments, and relatively small incremental rates.

4. An apparatus as defined in claim 1, wherein the magnetic brake is adjustable to allow controlled payout of the cable from the supply spool while limiting the maximum tension in the cable, and to allow payout of the cable at varying relatively small increments, and relatively small incremental rates.

5. An apparatus as defined in claim 2, wherein the counterweight sheave weighs on the cable to remove slack and maintain a minimum tension in the cable.

6. An apparatus as defined in claim 5, wherein the magnetic brake and the counterweight sheave act in unison to limit the range of tension in the cable, thereby minimizing stick-slip behavior, which allows smooth payout of cable from the supply spool.

7. An apparatus as defined in claim 1, wherein the manner in which cable payout is controlled enables the apparatus to monitor displacements of the anchor continuously and without interruption, over the available capacity of the supply spool, irrespective of rates of movement and accelerations of the anchor.

8. An apparatus as defined in claim 2, wherein the supply spool is connected to a first shaft that is rotatable about a first fixed axis, an encoder sheave is connected to a second shaft that is rotatable about a second fixed axis and the cable extends about the encoder sheave such that movement of the cable causes rotation of the encoder sheave and the second shaft about the second fixed axis, and the counterweight sheave is connected to a third shaft that is rotatable about a movable third axis that is suspended by the cable between the supply spool and the encoder sheave in a manner that provides tension in the cable during payout of the cable, and wherein the magnetic brake is disposed on the first shaft and the sensor comprises an encoder associated with the second shaft to detect movement of the second shaft.

9. An apparatus as defined in claim 8, wherein the magnetic brake and the encoder are disposed in an enclosure that is sealed against ambient conditions to a NEMA 4 rating and the supply spool and encoder sheave are located on the outside of the enclosure.

10. An apparatus as defined in claim 8, wherein the counterweight sheave that is rotatable about a movable third shaft is supported for movement along a vertical support that can move relative to the first and second shafts, wherein the first and second shafts are substantially at the same vertical height, and the bottom of the counterweight sheave takes up slack as it maintains tension in the cable, and the counterweight sheave can take up slack and maintain tension in a length of cable that is up to twice the range of movement of the counterweight sheave along the vertical support.

11. An apparatus as defined in claim 10, wherein the counterweight sheave is rotatably supported on a third shaft that can slide along the vertical support, and wherein the cable is wrapped about the counterweight sheave and the counterweight sheave rotates about the third shaft to allow the cable to move past the counterweight sheave.

12. An apparatus as defined in claim 11, wherein the spacing between the first and second axes is related to the diameter of the counterweight sheave in a manner designed to enable the counterweight sheave to move along the vertical support while providing substantially parallel orientation of the cable on opposite sides of the counterweight sheave over the full range of movement of the counterweight sheave along the vertical support, thereby maintaining a uniform minimum tension in the cable between the supply spool and the second end.

13. An apparatus as defined in claim 2, wherein the magnetic brake is adjustable to allow controlled payout of the cable from the supply spool while limiting the maximum tension in the cable, and to allow payout of the cable at incremental rates in the range of 0.00006 RPM to 0.02 RPM.

14. An apparatus as defined in claim 1, wherein the magnetic brake is adjustable to allow controlled payout of the cable from the supply spool while limiting the maximum tension in the cable, and to allow payout of the cable at incremental rates in the range of 0.00006 RPM to 0.02 RPM.

15. An apparatus as defined in claim 1, wherein the magnetic brake includes a shaft that is attached to the supply spool by means of a drive plate so that the supply spool, drive plate, and shaft rotate together and the shaft is part of the magnetic brake, and wherein the magnetic brake is connected directly with the shaft to apply the braking force directly to the supply spool.

16. An apparatus for use in a movement monitoring system, comprising a cable supply spool and a cable having first and second ends, the cable being wound about the supply spool at the first end and connected at the second end to an anchor such that the cable can be tensioned between the supply spool and the anchor and movement of the cable past a sensor can be used to monitor movement of the anchor relative to the supply spool, the supply spool is attached to a shaft by means of a drive plate that is connected directly to the shaft so that the supply spool, drive plate, and shaft rotate together to allow payout of the cable from the supply spool, and the cable payout rate from the supply spool being controlled by a magnetic brake that is fixed to the shaft and is configured to provide a predetermined constant non-frictional braking force directly on the supply spool, and wherein the magnetic brake is adjustable to allow controlled payout of the cable from the supply spool while limiting the maximum tension in the cable, and to allow payout of the cable at varying relatively small increments, and relatively small incremental rates.

* * * * *